United States Patent [19]

Smith

[11] Patent Number: 4,942,258

[45] Date of Patent: Jul. 17, 1990

[54] PROCESS FOR PREPARATION OF METHACRYLIC ACID WITH REGENERATION OF CATALYST

[75] Inventor: Thomas G. Smith, Naperville, Ill.

[73] Assignee: Amoco Corporation, Chicago, Ill.

[21] Appl. No.: 180,304

[22] Filed: Apr. 12, 1988

Related U.S. Application Data

[63] Continuation of Ser. No. 40,302, Apr. 20, 1987, abandoned, which is a continuation of Ser. No. 624,048, Jun. 25, 1984, abandoned.

[51] Int. Cl.$^5$ ..................... C07C 51/353; C07C 57/04
[52] U.S. Cl. ........................................ 562/599; 502/38; 502/49; 502/52
[58] Field of Search .................... 562/599; 502/38, 52, 502/49

[56] References Cited

U.S. PATENT DOCUMENTS

| | | | |
|---|---|---|---|
| 1,678,626 | 7/1928 | Jaeger | 502/38 |
| 2,162,893 | 6/1939 | Kuhl | 502/38 |
| 2,198,195 | 4/1940 | Groll et al. | 502/38 |
| 2,641,582 | 6/1952 | Haensel | 502/49 |
| 3,051,747 | 8/1962 | Leathers et al. | 562/599 |
| 3,933,888 | 1/1976 | Schlaefer | 562/599 |

FOREIGN PATENT DOCUMENTS

| | | | |
|---|---|---|---|
| 721773 | 11/1965 | Canada | 562/599 |
| 315412 | 9/1929 | United Kingdom | 502/38 |

*Primary Examiner*—Vivian Garner
*Attorney, Agent, or Firm*—Reed F. Riley; William H. Magidson; Ralph C. Medhurst

[57] ABSTRACT

Process is disclosed for regeneration of a solid methacrylic acid catalyst wherein said catalyst is decoked in the presence of an oxygen-containing gas at an initial temperature no greater than 650° F. and then by increasing the temperature incrementally to complete the regeneration at a temperature of from about 650° F. to 800° F.

2 Claims, No Drawings

PROCESS FOR PREPARATION OF METHACRYLIC ACID WITH REGENERATION OF CATALYST

This is a continuation of application Ser. No. 040,302, filed Apr. 20, 1987, now abandoned, which in turn is a continuation of Ser. No. 624,048, filed June 25, 1984, now abandoned.

FIELD OF THE INVENTION

The field of this invention relates to a process of producing an alpha-, beta-ethylenically unsaturated carboxylic acid compound which comprises (1) feeding a saturated aliphatic monocarboxylic acid compound and formaldehyde to a reactor, (2) condensing under vapor phase conditions said saturated monocarboxylic acid compound and formaldehyde to produce an alpha-, beta-ethylenically unsaturated monocarboxylic acid compound of one more carbon atom than said saturated carboxylic acid compound in the presence of a solid catalyst, (3) after coke is deposited on said solid catalyst in said reactor, stopping the feed of aliphatic monocarboxylic acid compound and formaldehyde compound to said reactor and decoking said catalyst by passing dilute oxygen over said catalyst at a temperature no greater than 650° F., preferably no greater than 550° F., while holding the exotherm to about 10 to 30° F., increasing the oxygen content incrementally while holding the exotherm to about 10 to 30° F. until there is no exotherm with a mixture of about 20% oxygen and 80% inert gas, e.g. air, followed by incrementally raising the temperatures by 25 to 75° F. and controlling the exotherm to about 10 to 30° F. until decoking is completed at about 650 to 800° F.

In more specific terms, the field of this invention relates to a process for producing methacrylic acid in one or more reactors from propionic acid and formaldehyde in a vapor-phase aldol-type condensation reaction in the presence of a solid catalyst wherein, after coke is deposited on the solid catalyst in a first reactor, the propionic acid-formaldehyde feed is diverted to a second reactor, or stopped entirely, and dilute oxygen is passed over the coked solid catalyst at a temperature of less than 550° F. to decoke the said catalyst. The solid catalyst preferably comprises at least one cation of a Group I or Group II metal and silica support, said support preferably having a surface area of 20 to 275 m$^2$/g, a pore volume of 0.1 to 0.8 cc/g and an average pore diameter of 75Å to 200Å.

BACKGROUND OF THE INVENTION

Unsaturated acids, such as methacrylic and acrylic acids, acrylonitrile, and the esters of such acids, such as methyl methacryate, are widely used for the production of corresponding polymers, resins and the like. Various processes and catalysts have been proposed for the conversion of alkanoic acids, such as acetic acid or propionic acid, and formaldehyde to the corresponding unsaturated monocarboxylic acids, e.g., methacrylic acid, by an aldol-type reaction. Generally, the reaction of acid and formaldehyde takes place in the vapor or gas phase while in the presence of a basic or acidic catalyst.

The literature is replete with disclosures of the reaction of aliphatic carboxylic acid compounds with formaldehyde to produce alpha-, beta-ethylenically unsaturated aliphatic monocarboxylic acid compounds of one more carbon atom than the saturated carboxylic acid compounds.

Kirk-Othmer in Volume 15, 3rd Edition (1981) at pages 364 and 374 indicates that the propionate-formaldehyde route has been considered in the preparation of methacrylic acid or methyl methacrylate. Kirk-Othmer states that a suitable catalyst must provide high selectivity and high conversion and have at least 6 months life. Effective catalysts include alkali metal or alkaline earth metal aluminosilicates, potassium hydroxide or cesium hydroxide treated pyrogenic silica, alumina and lanthanum oxide. While Kirk-Othmer indicates that the results cover a range of conversions and selectivities and that generally best results are at conversions of about 50% with selectivities of more than 80%, these conversions and selectivities appear to be excessively high unless Kirk-Othmer is referring to processes using a substantial molar excess of propionic acid to formaldehyde and the conversions and selectivities are based on formaldehyde. When propionic acid is employed in a molar equivalency with formaldehyde, and the conversions and selectivities are based upon propionic acid, both selectivities and percent conversions are low. A careful review of the art by us fails to disclose any examples in the prior art of operations where the reaction has been on stream for more than a day or two. This is not surprising since our experience has shown that catalyst life is generally low and there is a tendency for coke deposition on the catalyst with the result that the catalyst activity drops rapidly. It is not uncommon for coke deposition to reach unacceptable levels in 24 to 48 hours.

Our studies of the surfaces of coked catalysts have demonstrated that deposition of coke decreases the activity of certain areas of the catalyst surface but not other areas, that the continuing catalytic activity depends not only on the amount of coke deposited on the catalyst surface but also the composition of the catalyst. Although a 2 to 3 grams of a coked silica catalyst bed can be regenerated with air at 1000° F., larger beds of coked silica catalysts are sintered under these regeneration conditions.

Our studies have shown that when using approximately equal molar concentrations of propionic acid and formaldehyde, that silica supported catalysts provide a relatively high degree of conversion and selectivity based on propionic acid. In general, the higher the reaction temperature, the greater the percent conversion of the propionic acid and the lower the selectivity of the catalyst. Our studies have also shown that silica supports tend to degrade over a period of time in the sense that the surface area of the catalyst decrease while the average pore size increases. As the surface area drops to about 10 to 20 m$^2$/g and the number of pores having a diameter less than 1200Å decreases, catalyst activity falls off rapidly. This degradation is also a function of the water content of the reaction media. The more water present, the faster the degradation of the silica gel support. While substantially anhydrous reactants can be employed, there is one molecule of water produced per molecule of product. Further, there is a tendency for the alkali metal or alkaline earth metal cation to be volatilized off from the catalyst support with the result that catalyst activity (percent conversion and/or percent selectivity) decreases rapidly.

As pointed out by Kirk-Othmer there is a need for a catalyst system which permits operation for longer periods of time While Kirk-Othmer states that the catalyst life should be at least 6 months, we know of no prior art examples that disclose condensation reaction for more than 24 to 48 hours. Accordingly, there is a need for a suitable catalyst and/or process for the conversion of propionic acid compound to methacrylic acid compound which can be utilized for extended periods of time without substantial degradation of the catalyst.

The general object of this invention is to provide a new catalyst regeneration process suitable for use in the catalytic condensation of a saturated aliphatic monocarboxylic acid compound and formaldehyde compound to alpha-, beta-ethylenically unsaturated monocarboxylic acid compound. Other objects appear hereinafter.

The objects of this invention can be attained by a process of producing an alpha-, beta-ethylenically unsaturated carboxylic acid compound which comprises (1) feeding a saturated aliphatic monocarboxylic acid compound and formaldehyde to a reactor, (2) condensing under vapor phase conditions said saturated monocarboxylic acid compound and formaldehyde to produce an alpha-, beta-ethylenically unsaturated monocarboxylic acid compound of one more carbon atom than said saturated carboxylic acid compound in the presence of a solid catalyst, (3) after coke is deposited on said solid catalyst in said reactor, stopping the feed of aliphatic monocarboxylic acid compound and formaldehyde compound to said reactor and decoking said catalyst by passing dilute oxygen over said catalyst at a temperature no greater than 650, preferably no greater than 550° F., while holding the exotherm to about 10 to 30° F., increasing the oxygen content incrementally while holding the exotherm to about 10 to 30° F. until there is no exotherm with a mixture of about 20% oxygen and 80% inert gas, e.g. air, followed by incrementally raising the temperatures by 25 to 75° F. and controlling the exotherm to about 10 to 30° F. until decoking is completed at about 650 to 800° F.

By controlling the exotherm during regeneration, it is possible to prevent loss of the cations and/or sintering of the catalyst bed and reduce changes in the pore structure and surface area of the silica catalyst. Accordingly, the catalyst can be used repeatedly after numerous regenerations.

On a commercial basis, the process can be carried out advantageously by diverting the flow of alpha, betaethylenically unsaturated monocarboxylic acid compound and formaldehyde from the first reactor to a second reactor while the first reactor is undergoing regeneration. In those cases where regenerations are carried out for half as long as the aldo-type condensation is being carried out, it is possible to employ 3 reactors and 2 downstream processing sections with one reactor undergoing regeneration and 2 reactors producing alpha-, beta-ethylenically unsaturated monocarboxylic acid compound.

Briefly, the silica supports of this invention can be prepared by gelling an aqueous silica colloid, drying the composition to remove substantially all of the moisture other than the water of hydration, and calcining.

The alkali metal and/or alkaline earth metal cations of the catalyst can be used in a concentration of 0.001 to 0.2 equivalents (gram atoms) of cation per 100 grams of silica support on a dry solids basis. In general, it is preferred to have from about 0.004 to 0.1 equivalents of cation per 100 grams of silica support on a dry solids basis since the higher the concentration of cation, the lower the temperature needed for condensation of the saturated aliphatic monocarboxylic acid compound and formaldehyde compound and the greater the selectivity and life of the catalyst. The lower the concentration of the cation, the higher the condensation temperature necessary to obtain the desired degree of conversion to alpha-, beta-ethylenically unsaturated monocarboxylic acid compound and the lower the selectivity of catalyst and life of the catalyst.

Suitable sources of alkali metal and alkaline earth metal cations include sodium hydroxide, potassium hydroxide, cesium hydroxide, lithium hydroxide, rubidium hydroxide, strontium hydroxide, magnesium hydroxide, lithium phosphate, trisodium phosphate, cesium phosphate, sodium borate, barium hydroxide, sodium carbonate, cesium fluoride, cesium nitrate, etc. Of these, the alkali metal cations are preferred.

While any commercially available colloidal silica can be used, it is preferred to use commercially available colloidal silicas having an average particle diameter of 40 to 1000Å particularly those having a particle diameter of about 50 to 250Å in order to produce silica supported catalysts having a surface area of 20 to 275 $m^2/g$, a pore volume of 0.1 to 0.8 c.c./g and an average pore diameter of about 75 to 200Å, which are the subject of copending Ser. No. 624,040 filed on even date in the name of Hagen et al, now abandoned which is hereby incorporated by reference. As pointed out in Ser. No. 624,056, silica catalysts comprising at least one cation of a Group I or Group II metal of the Periodic Table of Elements (inside back cover, Handbook of Chemistry & Physics, 46th Ed., Chemical Rubber Co., Cleveland, Ohio) and silica support, said support having a surface area of 20 to 275 $m^2/g$, pore volume of 0.1 to 0.8 cc/g and an average pore diameter of 75 to 200Å, have relatively high activity (% conversion and selectivity) and relatively long life. Pore volume, surface area and average pore diameter are interdependent variables. Other things being equal, holding one variable constant, as the surface area increases, pore volume increases; as the surface area increases, average pore diameter decreases and; as the pore volume increases, average pore diameter increases. It is critical in Ser. No. 624,040 that the catalyst satisfy each of the pore volume, surface area and average pore diameter requirements. For example, if the catalyst has a porosity greater than 0.8 cc/g, the catalyst lacks the strength to resist attrition necessary for use over extended periods of time. If the porosity is less than 0.1 cc/g, the surface area is too low and/or the average pore diameter is too high. However, as explained above, the catalyst loses activity as it loses pores having a diameter under 1200Å. Accordingly, it is desirable to use a catalyst having a substantially smaller average pore diameter to insure that the catalyst has adequate life. If the average pore diameter of the starting catalyst is substantially higher than 200Å, there is a substantial decrease in the life of the catalyst. Pore diameters of at least 75Å are necessary in order to permit gas diffusion of the reactants and reaction products.

The silica can be treated either prior to drying or after calcination with cations. Catalysts prepared by the addition of the cations to the colloidal silica before or during gelation can be viewed as coformed catalysts which are the subject of application Ser. No. 624,041 filed on even date in the name of Kaduk et al, now abandoned, which is hereby incorporated by reference. As pointed out in application Ser. No. 624,041, coformed catalysts are advantageous in the sense that they are substantially more water tolerant than catalysts prepared by the treatment of the calcined silica with an aqueous solution of the cation and they are easier to decoke since, other things being equal, they do not exotherm as much as catalysts prepared by impregnation. This is apparently due to the more uniform distribution of the cations in the support.

The silica supports of this invention are preferably prepared by forming an aqueous composition comprising about 20 to 60% by weight colloidal silica on a dry basis and alkali metal and/or alkaline earth metal cation. The colloidal silica is gelled by adjusting the pH to a range of about 3 to 10, preferably about pH 6.0 to about 9.0, preferably with alkali metal or alkaline earth metal cations. Salts such as $NH_4NO_3$ can be used to accelerate gellation. While silica hydrogels can be aged for two weeks or more, aging seems to have no effect on the properties of the catalyst and accordingly, aging is not necessary. The composition is then dried by any suitable means, such as in a microwave oven, to constant weight and apparent dryness, e.g., about 4 to 5% moisture on a dry solids basis. Apparently only the water of hydration is retained by the silica gel after drying to constant weight. The silica gel is then calcined at about 300 to 800° C., preferably about 300 to 600° C. As pointed out in Ser. No. 624,040 at calcination temperatures above about 800° C., there is a tendency for the surface area to go down, the pore volume to go down and the pore diameter to go up with the result that the catalyst is outside the ranges required in Ser. No. 624,040. However, such catalysts can be used in this invention.

The process of this invention can be used for the aldol-type condensation of saturated aliphatic monocarboxylic acid compounds to alpha, beta-ethylenically unsaturated monocarboxylic acid compounds of one more carbon atom than the starting saturated aliphatic carboxylic acid compound. Suitable aliphatic monocarboxylic acid compounds that can be converted in the aldol-type condensation reaction include acetic acid, propionic acid, methyl acetate, methyl propionate, ethyl propionate, acetonitrile, propionitrile, etc. The preferred saturated monocarboxylic acid compounds are propionic acid compounds and particularly propionic acid since the catalyst of this invention has been designed primarily for large scale production of methacrylic acid.

While any suitable source of formaldehyde compound can be used, such as formalin, paraformaldehyde, methanolic formaldehyde, trioxane, etc., it is preferred to use substantially anhydrous formaldehyde, particularly cracked monomeric gaseous, substantially anhydrous formaldehyde.

Briefly, an alpha-, beta-ethylenically unsaturated monocarboxylic acid compound can be prepared by condensing under vapor phase conditions a saturated aliphatic monocarboxylic acid compound and formaldehyde compound in the presence of a silica catalyst having at least one cation of a Group I or Group II metal in a concentration of about 0.001 to 0.2 equivalents per 100 grams silica support on a dry solids basis, preferably one comprising a support having a surface area of 20 to 275 m$^2$/g, a pore volume of 0.1 to 0.8 cc/g and an average pore diameter of 75 to 200Å.

This reaction can be carried out advantageously in the presence of a water-immiscible hydrocarbon or halohydrocarbon diluent of from about 6 to 12 carbon atoms having an azeotropic boiling point of about 95° C. or less, which is the subject of co-pending Ser. No. 624,050, in the name of Smith filed on even date, now U.S. Pat. No. 4,736,062 which is hereby incorporated by reference.

Because the product stream contains amounts of unreacted propionic acid and unreacted formaldehydes as well as water, selection of a suitable hydrocarbon in a preferred method of operation wherein reactor effluent is distilled to separate the components is determined by the boiling points of azeotropes of propionic acid and methacrylic acid. Both propionic acid and methacrylic acid form water azeotropes which boil at approximately 99° C. Separation by distillation of the $C_6$ to $C_{12}$ hydrocarbon in the presence of water requires that the water:hydrocarbon azeotrope which forms have a boiling point below the boiling points of the propionic acid and methacrylic acid and water azeotropes. Preferably, the boiling point of the water:hydrocarbon azeotrope be no more than 95° C.

Boiling points and percent water of typical hydrocarbon:water azeotropes are:

| Hydrocarbon | % Water | B. P. °C. |
|---|---|---|
| n-Hexane | 5 | — |
| n-Heptane | 13 | 79 |
| n-Octane | 23 | 90 |
| n-Nonane | 40 | 95 |

Branched $C_6$ to $C_{12}$ saturated alphatic hydrocarbons, aromatic hydrocarbons of 6 to 12 carbon atoms, cycloalkanes of 6 to 12 carbon atoms and mixtures thereof which form water:hydrocarbon azeotropes with boiling points of no more than 95° C. can be also used.

As pointed out in Ser. No. 624,050, a diluent is advantageous in increasing the percent product yield by approximately 3 (mole) % without any loss of selectivity of the catalyst. Further, as explained below, the diluent has additional functions in the overall unitary process for producing methacrylic acid from propionic acid. Suitable diluents include n-hexane, n-heptane, n-octane, 2-ethylhexane, n-decane, n-dodecane, o,p or m-xylene, benzene, toluene, cycloalkanes and mixtures thereof. The concentration of diluent can range from about 10 to 50% by weight of the reactants in the main reactor.

The molar ratio of monocarboxylic acid compound to formaldehyde can range from 25:1 to 1:25. However, best results with this catalyst in the production of methacrylic acid can be obtained using a molar ratio of propionic acid compound to formaldehyde of from about 0.5–2.0 to 1. In general the lower the molar ratio, the higher is the percent conversion based upon the amount of propionic acid converted.

While the aldol-type condensation can be carried out at about 280 to 500° C., it is preferred to operate at about 280 to 350° C. since selectivity goes up as the reaction temperature goes down. As pointed out in copending application Ser. No. 623,945 filed in the name of Smith et al on even date, now abandoned, which is hereby incorporated by reference, (1) the amount of undesirable unsaturated cyclic ketone by-product which is a catalyst for the polymerization of alpha, beta-ethylenically unsaturated monocarboxylic acids can be reduced from 4 mol % based on starting propionic acid compound at 390° C. to approximately 2.5 mol % at 350° C. or less (about 1% at 325° C.) or (2) over a 80 day period of alternate 24 hour periods of condensation followed by 24 hour periods of decoking that the loss of cation can be reduced from over 75% at 390° C. with attendant loss of catalytic activity to about 10% at 350° C. with constant activity.

In somewhat greater detail, the unitary process for the production of methacrylic acid comprises (1) feeding propionic acid and formaldehyde compound to a reactor, containing the silica catalyst (2) condensing under vapor phase conditions formaldehyde and propionic acid to produce a composition comprising water, formaldehyde, propionic acid and methacrylic acid, (3) distilling said reaction product to remove water, unreacted formaldehyde and at least some of the propionic acid from the reaction product, (4) contacting the distillate with an entraining agent comprising a water immiscible diluent having an azeotropic boiling point of about 95° or less in the distillation column to remove water and at least some of the formaldehyde overhead.

In a still more preferred version of this process, a side draw is located at least part way up the distillation column to remove a composition comprising propionic acid and formaldehyde. The use of a side draw is disclosed, and claimed in co-pending Ser. No. 624,049 filed in the name of Baleiko et al, now U.S. Pat. No. 4,599,144, which is hereby incorporated by reference. As pointed out in Ser. No. 624,049, the side draw facilitates the removal of part of the formaldehyde from the aqueous mixture going overhead and thereby precludes polymerization of formaldehyde at the top of the distillation column thereby eliminating or reducing the possibility of plugging at the top of the distillation column. Irrespective of whether a side draw is employed or not, it is contemplated that the formaldehyde is recovered from the aqueous formaldehyde taken overhead by reacting the aqueous formaldehyde with a commercially available alcohol such as 2-ethylhexanol to form a hemiacetal, distilling water from the hemiacetal and then cracking the substantially anhydrous hemiacetal to recover the formaldehyde. The formaldehyde is advantageously separated from the alcohol by adding a water immiscible diluent having an azeotropic boiling point of about 95° or less at the top of the column in order to facilitate the removal of the formaldehyde from the alcohol used to form the hemiacetal. The formaldehyde and diluent are then recycled to the main reactor.

The process of this invention can be carried out at a weight hourly space velocity (WHSV) of about 0.1 to 10, preferably 0.5 to 6.5. In general the lower the weight hourly space velocity the lower the reaction temperature necessary. The higher the weight hourly space velocity the higher the reaction temperature necessary.

The catalysts are decoked after about 12 to 72 hours on stream. In order to prevent sintering of the silica gel, dilute oxygen (1 to 5% by volume and 95 to 99% by volume inert gas) is contacted with the catalyst bed at about 450 to 650° F., preferably 450 to 550° F. while holding the exotherm to about 10 to 30° F., increasing the oxygen content incrementally while holding the exotherm to about 10 to 30° F. until there is no exotherm with a mixture of about 20% oxygen and 80% inert gas, e.g. air, followed by incrementally raising the temperatures by 25 to 75° F. and controlling the exotherm to about 10 to 30° F. until decoking is completed at about 650 to 800° F.

In general, this invention relates to a process for production of alpha-beta-ethylenically unsaturated carboxylic acid compound which comprises (1) feeding a saturated aliphatic monocarboxylic acid compound and formaldehyde to a reactor, (2) condensing under vapor phase conditions said saturated monocarboxylic acid compound and formaldehyde to produce an alpha-beta-ethylenically unsaturated monocarboxylic acid compound of one more carbon atom than said saturated carboxylic acid in the presence of a solid catalyst at a temperature of from about 280° C. to about 500° C., (3) after coke is deposited upon said solid catalyst, stopping the feed of said aliphatic monocarboxylic acid compound and formaldehyde compound to said reactor and decoking said catalyst by passing an oxygen-containing gas over said catalyst at a temperature no greater than about 800° F., and repeating steps (1) and (2).

In more specific terms, this invention relates to a process of producing an alpha-, beta-ethylenically unsaturated carboxylic acid compound which comprises (1) feeding a saturated aliphatic monocarboxylic acid compound and formaldehyde to a reactor, (2) condensing under vapor phase conditions said saturated monocarboxylic acid compound and formaldehyde to produce an alpha-, beta-ethylenically unsaturated monocarboxylic acid compound of one more carbon atom than said saturated carboxylic acid compound in the presence of a solid catalyst, (3) after coke is deposited on said solid catalyst in said reactor, stopping the feed of aliphatic monocarboxylic acid compound and formaldehyde compound to said reactor and decoking said catalyst by passing dilute oxygen over said catalyst at a temperature no greater than 650° F., while holding the exotherm to about 10 to 0° F., increasing the oxygen content incrementally while holding the exotherm to about 10 to 30° F. until there is no exotherm with a mixture of about 20% oxygen and 80% inert gas, e.g. air, followed by incrementally raising the temperatures by 25 to 75° F. and controlling the exotherm to about 10 to 30° F. until decoking is completed at about 650 to about 800° F.

In the examples that follow, percent conversion, percent yield and percent selectivity are all based on propionic acid (PA) unless otherwise stated.

EXAMPLE I

This example illustrates the production of methacrylic acid in a pilot plant reactor using a coformed cesium phosphate silica gel catalyst having a surface area of 119 m$^2$/g, porosity of 0.604 cc/g and an average pore diameter of 168Å containing 1.97 weight percent cesium based on the dry weight of the silica. A slurry of 29 parts by weight paraformaldehyde, 106 parts by weight propionic acid (PA:FA molar ratio 3:2) and 47 parts by weight heptane was continuously vaporized to thermally decompose the paraformaldehyde to monomeric formaldehyde at 400° F. The composition was then conveyed to a reactor system comprising a 1 inch outside diameter by 0.834 inch inside diameter by 6 foot Inconel tube equipped with 0.25 inch outside diameter thermowell having a 4 foot long catalyst zone containing 200 grams of catalyst and on each side of the catalyst a 1 foot zone of Denstone packing. The thermowell was equipped with thermocouples inserted at 6 inch intervals and electrical heating means were positioned along the reactor. Conversion of propionic acid and formaldehyde to methacrylic acid was carried out for 24 hours while maintaining the pilot plant reactor at 660° F. (350° C.) 10 psig and a weight hourly space velocity (WHSV) of 1.55. The reaction product was collected in a heat exchanger and condensed. After 24 hours, feed to the reactor was turned off and the reactor temperature was reduced to 550° F. Two percent oxygen in nitrogen was added slowly to the reactor in order to limit the exotherm during decoking to about 20° F. After that exotherm passed, the oxygen content was increased to 10% and after that exotherm was limited to 20° F., the nitrogen oxygen mixture was replaced with air. After each exotherm passed the temperature of the reactor was raised by 50° F. increments by closely controlling the exotherm until the reactor was at 700° F. This decoking process typically takes 2 to 4 hours. Air was continuously flowed through the reactor at 700° F. for a total of 24 hours. The air was turned off and the reactor temperature was reduced to 660° F. and the condensation of propionic acid and formaldehyde was begun. The sequential condensation and decoking operation was carried out for 80 days of which 40 days were methacrylic acid production and 40 days decoking. The molar ratio of PA:FA was varied from 1.5:1 to 1.34:1. The physical properties of the catalyst before and after the 80 days onstream is set forth below in Table 1. The yield after the first day and the average for the first 66 days is set forth below in Table 1.

TABLE 1

|  | Initial Catalyst and First Day Analysis of Products | Final Catalyst and Average Analysis of Products Over First 66 Days |
|---|---|---|
| Cesium Content | 1.97 wt. % | 1.76 wt. % |
| Surface Area | 119 m²/g | 59 m²/g |
| Pore Volume | 0.604 cc/g | 0.570 cc/g |
| Average Pore Diameter | 168 Å | 302 Å |
| Molar Ratio of PA:FA | 1.5 | 1.34 |
| Conversion Based on PA | 32.1% | 32.1% |
| Selectivity Based on PA | 91.3% | 85.9% |
| MA/PA Yield | 29.3% | 27.6% |
| Conversion Based on FA | 51.9% | 50.0% |
| Selectivity Based on FA | 84.9% | 74.2% |
| MA/FA Yield | 44.1% | 37.1% |

The catalyst employed in this example was prepared by intensely stirring a solution of 10302.9 grams Nalcoag, 1034-A colloidal silica (34% solids, 200Å particle diameter) and a solution of 111.66 grams cesium phosphate (having an average of 5 waters of hydration per molecule of cesium phosphate) in 500 cc deionized water. After intense stirring for 10 minutes a solution of 100 grams ammonium nitrate in 150 grams deionized water was added to the sol and the mixture was stirred for 2 minutes at which time it began to thicken. The silica gel was permitted to harden after standing at room temperature overnight. The gel was dried in a microwave oven to constant weight and size to 20 to 40 mesh and calcined according to the following increments 2 hours at 165° C., followed by increasing the temperature gradually to 540° C. over 4 hours and then maintaining at 540° C. for an additional 8 hours. All of the steps were carried out in flowing air.

EXAMPLE II

A 200 ml sample of commercial colloidal silica, Ludox (Trademark) AS-40 Brand, E. I. du Pont de Nemours & Co. (Inc.), Industrial Chemicals Dept., Wilmington, Del. was placed in a beaker. Temperature was 25° C. The material was an aqueous colloidal dispersion of silica particles having a high specific surface area. Characteristics were as follows: specific surface area, m²/g 130; av. particle diameter, mm 21; silica (as $SiO_2$) 40 wt%; pH (25° C.) 8.0. With stirring, the pH of the sample was lowered from about 10.5 to 3.0 by dropwise addition of concentrated nitric acid (0.16 N). The pH was then raised to about 6.0 by the dropwise addition of concentrated ammonium hydroxide (0.15 N). The mixture was thereupon stirred for 8 hours, at a temperature of 25° C., at which time a thick gel had formed. The gel was dried for 2 hours in a drying oven at a temperature of 120° C., then crushed and sieved to 18/40 mesh granules (U.S. sieve). The resulting catalyst support, was then calcined for 16 hours at a temperature of 525° C. Analysis by A.A. spectroscopy was: 400 ppm aluminum, 2100 ppm sodium, and <100 ppm zirconium, <100 ppm titanium, <200 ppm iron by Edax spectroscopy.

A solution of trisodium phosphate was added to the above catalyst support, using the incipient wetness technique. The resulting catalyst had a loading of 6000 ppm of sodium.

The reactor system consists of a 1 inch O.D.×0.834 inch I.O.D.×6 feet heated Inconel tube equipped with a 0.25 inch O.D. thermowell. The catalyst zone is typically 4 feet in length and typically contains 200 gms of catalyst. Thermocouples inserted into the thermowell measure and control temperature at 6 inch intervals. The feed system is designed to handle a propionic acid paraformaldehyde slurry. The slurry is pumped to a vaporizer in which the paraformaldehyde is thermally decomposed to monomeric formaldehyde at 400° F. This system allows the use of lower reactor temperatures than a feed system using trioxane and propionic acid since the trioxane does not completely decompose to monomeric formaldehyde below a temperature of 750° F.

Reaction conditions were: contact time 3.2 seconds; reaction temperature 390° C. (734° F.).

The reactor was loaded with 24 inches (103.1 gm) of 4-8 mesh (U.S. Standard) (⅛") AS-40 trisodium phosphate prepared as above having a loading of 6000 ppm sodium. A two-day run was carried out with a propionic acid: formaldehyde ratio of 1:1. The catalyst was then regenerated as follows:

At a temperature of 550° F., a low flow rate of air, 0.05 SCFH, together with 0.5 SCFH of nitrogen, was fed to the reactor, resulting in a broad, low-amplitude exotherm of about 20° F. The nitrogen flow was then gradually reduced while increasing the temperature in increments of 20° F., to 650° F., followed by 50° F. increments to 750° F. There were no exotherms exceeding 30° F during this procedure. The catalyst was then regenerated for 48 hours at 750° F. Following regeneration, the reactor conditions used during the previous two-day run were repeated. Results are shown in Table 2. Table 2 indicates that the mild regeneration has only a minor effect on catalyst performance.

TABLE 2

| EFFECT OF MILD REGENERATION ON CATALYST PERFORMANCE | | |
|---|---|---|
|  | Before | After |
| PA Conversion % | 37.3 | 37.0 |
| MA Selectivity, Mole % | 58.4 | 55.5 |
| MA Yield, Mole % | 21.8 | 20.8 |
| Hours on Stream Since Decoking | 4 | 5 |

Note:
All results were obtained at 734° F. (390° C.), 3.2 seconds contact time, and 1:1 PA/FA using 4–8 mesh, 6000 ppm Na, $Na_3PO_4$ silica gel catalyst. Selectivities and yields are based on PA.

The regeneration procedure was repeated but using air at 1000° F. Large exotherms resulted. At an air flow of 250 ml/min and a temperature of 1000° F., during the first 10 minutes the front part of the catalyst bed experienced an exotherm of 430° F. The rate of temperature rise during this exotherm was also large, about 30° F./min. The end of the bed had an exotherm of 350° F., resulting in a maximum temperature of 1350° F. This occurred after 2 hours on air.

Catalyst performance before and after decoking is shown in Table 3. The data show a large drop in yield after decoking, for both 6-8 and 18-40 mesh catalyst. By-products also increased. The catalyst used for these experiments was a $Na_3PO_4$ catalyst containing 6700 ppm Na and prepared via incipient wetness. The catalyst was subsequently removed from the reactor in three sections and analyzed. The three catalyst cuts contained 3500 ppm, 6800 ppm, and 17,600 ppm, as compared with the initially uniform bed concentration of 6700 ppm. Changes in the pore structure of the silica gel probably took place as well. Results are in Table 3.

TABLE 3

RESULTS FOR RUNS 1 AND 2

| Run No./Sparge No. | $C_{PA}$ | $S_{PA}$ | $Y_{PA}$ |
|---|---|---|---|
| 1-1/1 | 36.5 | 65.1 | 23.8 |
| 1-2/2 | 29.7 | 77.8 | 23.1 |
| 1-3/3 | 29.0 | 70.3 | 20.4 |
| 48 hr regeneration | | | |
| 1-4/4 | 11.5 | 56.9 | 6.6 |
| 1-5/5 | 13.6 | 85.7 | 11.5 |
| dropped 6-8 mesh | | | |
| loaded 18-40 mesh | | | |
| 2-1/6 | 40.2 | 59.1 | 23.7 |
| 2-2/7 | 36.5 | 66.4 | 24.2 |
| 48 hr regeneration | | | |
| 2-3/8 | 27.9 | 18.5 | 5.2 |

TABLE 3-continued

RESULTS FOR RUNS 1 AND 2

| Run No./Sparge No. | $C_{PA}$ | $S_{PA}$ | $Y_{PA}$ |
|---|---|---|---|
| 2-4/9 | 31.0 | 42.0 | 13.0 |

Note:
$C_{PA}$ is the percent conversion of propionic acid.
$S_{PA}$ is the mole percent selectivity to methacrylic acid based on the conversion of propionic acid.
$Y_{PA}$ is the mole percent yield of methacrylic acid based on the feed rate of propionic acid.

What is claimed is:

1. In a vapor-phase process for making methacrylic acid comprising combining in a reactor a feed containing propionic acid and formaldehyde in the presence of a solid catalyst comprising cesium cation and a silica support having a surface area of 20 to 275 $m^2/g$, a pore volume of 0.1 to 0.8 cc/g, and an average pore diameter of 75 to 200 Angstroms, the improvement comprising intermittently halting said feed to said reactor and decoking said catalyst by passing an oxygen-containing gas containing 1 to 5% by volume oxygen and 95 to 99% by volume inert gas over it at a temperature no greater than about 800° F., said decoking being performed at an initial temperature no greater than 650° F. and then by controlling the exotherm incrementally to a temperature no greater than about 800° F.

2. In a vapor-phase process for making methacrylic acid comprising combining in a reactor a feed containing propionic acid and formaldehyde in the presence of a solid catalyst comprising cesium cation and a silica support having a surface area of 20 to 275 $m^2/g$, a pore volume of 0.1 to 0.8 cc/g, and an average pore diameter of 75 to 200 Angstroms, the improvement comprising intermittently halting said feed to said reactor and diverting it to at least one other reactor for making said methacrylic acid and decoking said catalyst by passing an oxygen-containing gas containing 1 to 5% by volume oxygen and 95 to 99% by volume inert gas over it at a temperature no greater than about 800° F., said decoking being performed at an initial temperature no greater than about 450° F. to 550° F. and then by controlling the exotherm incrementally to a temperature no greater than about 800° F.

* * * * *

UNITED STATES PATENT OFFICE
CERTIFICATE OF CORRECTION

Patent No. 4,942,258   Dated July 17, 1990

Inventor(s) THOMAS G. SMITH

It is certified that error appears in the above-identified patent and that said Letters Patent is hereby corrected as shown below:

PATENT

| Column | Line | |
|---|---|---|
| 4 | 27 | "624,056" should read --624,040-- |
| 10 | 17 | "inch 1.0.D." should read --inch I.D.-- |

Signed and Sealed this

Twenty-seventh Day of August, 1991

Attest:

HARRY F. MANBECK, JR.

Attesting Officer   Commissioner of Patents and Trademarks